United States Patent
Kudo et al.

(10) Patent No.: US 10,331,818 B2
(45) Date of Patent: Jun. 25, 2019

(54) SIMULATION SYSTEM AND SIMULATION METHOD

(71) Applicant: HITACHI, LTD., Chiyoda-ku, Tokyo (JP)

(72) Inventors: Yasuyuki Kudo, Tokyo (JP); Kouji Fukuda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 195 days.

(21) Appl. No.: 15/324,966

(22) PCT Filed: Jul. 11, 2014

(86) PCT No.: PCT/JP2014/068584
§ 371 (c)(1),
(2) Date: Jan. 9, 2017

(87) PCT Pub. No.: WO2016/006101
PCT Pub. Date: Jan. 14, 2016

(65) Prior Publication Data
US 2017/0206290 A1    Jul. 20, 2017

(51) Int. Cl.
| | | |
|---|---|---|
| *G06F 17/11* | (2006.01) | |
| *G06F 17/18* | (2006.01) | |
| *G06F 17/50* | (2006.01) | |
| *G16H 50/50* | (2018.01) | |

(52) U.S. Cl.
CPC .......... *G06F 17/5009* (2013.01); *G06F 17/11* (2013.01); *G06F 17/18* (2013.01); *G06F 2217/16* (2013.01); *G16H 50/50* (2018.01)

(58) Field of Classification Search
CPC ...... G06F 17/5009; G06F 17/18; G06F 17/11; G06F 2217/16; G16H 50/50
USPC .............................................................. 703/2
See application file for complete search history.

(56) References Cited

U.S. PATENT DOCUMENTS

| | | | | |
|---|---|---|---|---|
| 7,949,501 | B1 * | 5/2011 | Iravani | G05B 19/41885 703/6 |
| 2004/0017574 | A1 | 1/2004 | Vuong et al. | |
| 2013/0179142 | A1 * | 7/2013 | Kim | G06F 17/5036 703/14 |

FOREIGN PATENT DOCUMENTS

| | | |
|---|---|---|
| JP | 2005-534192 A | 11/2005 |
| WO | WO 2004/013723 A2 | 2/2004 |

* cited by examiner

*Primary Examiner* — Saif A Alhija
(74) *Attorney, Agent, or Firm* — Miles & Stockbridge PC

(57) ABSTRACT

A first evaluation function for executing a simulation by calculating an evaluation value using a first parameter and second parameter having values is held, a first simulation is executed, a result group including evaluation values to which a predetermined phenomenon occurs is acquired from the evaluation values calculated by the first simulation, a start value and an end value of the first parameter for analyzing the phenomenon on the basis of the result group are acquired, a second simulation is executed by calculating evaluation values corresponding to the values of the first parameter from the start value to the end value using the values of the second parameter and the first evaluation function, and data for displaying the evaluation values calculated by the second simulation in such a manner as to be continuous with the evaluation values in the result group corresponding to the start value is output.

24 Claims, 8 Drawing Sheets

| ITEM | START TIME | END TIME | PARAMETERS | | | |
|---|---|---|---|---|---|---|
| | | | A | B | C | ... |
| MINIMUM VALUE | 0 | 100 | -5 | 0 | -5 | ... |
| MAXIMUM VALUE | | | 5 | 10 | 15 | ... |
| STRIDE | 1 | | 1 | 1 | 2 | ... |

INITIAL SETTING INFORMATION

| START TIME | T=40 | T=35 | T=30 |
|---|---|---|---|
| 401a RANKING LIST OF SENSITIVITY ANALYSIS | RANKING PARAMETERS<br>1  A(+0.50)<br>2  C(−0.33)<br>3  D(+0.30)<br>⋮ | RANKING PARAMETERS<br>1  A(+0.65)<br>2  C(−0.39)<br>3  D(+0.25)<br>⋮ | RANKING PARAMETERS<br>1  A(+0.75)<br>2  C(−0.42)<br>3  D(+0.20)<br>⋮ |
| 402a TIME SERIES GRAPH OF SECOND SIMULATION RESULT | | | |
| 403a SCATTER DIAGRAM OF PARAMETER SETTING CORRESPONDING TO REFERENCE | | | |

| | | | PARAMETERS | | | | REFERENCE | | |
|---|---|---|---|---|---|---|---|---|---|
| ITEM | START TIME | END TIME | A | B | C | ... | KF | KG | KH |
| MINIMUM VALUE | 25 | 50 | 1.5 | 2.5 | 4.0 | ... | 200 OR SMALLER | 20 ~ 40 | 5.0 OR SMALLER |
| MAXIMUM VALUE | 40 | | 2.5 | 3.5 | 6.0 | ... | | | |
| STRIDE | 1 | | 0.1 | 0.1 | 0.2 | ... | | | |

RESETTING INFORMATION
(EXAMPLE OF RESETTING OF SIMULATION #23)

| START TIME | T=30 | | |
|---|---|---|---|
| EVALUATION TIME | F | G | H |
| 401b RANKING LIST OF SENSITIVITY ANALYSIS | RANKING  PARAMETERS<br>1  A(+0.75)<br>2  C(-0.42)<br>3  D(+0.20)<br>:   : | | |
| 402b TIME SERIES GRAPH OF SECOND SIMULATION RESULT | Evaluation Value F, 200, time 25–50 | Evaluation Value G, 20–40, time 25–50 | Evaluation Value H, 5.0, time 25–50 |
| 403b SCATTER DIAGRAM OF PARAMETER SETTING CORRESPONDING TO REFERENCE | A: 1.5–2.5, C: 4.5–5.5 | A: 1.5–2.5, C: 4.5–5.5 | A: 1.5–2.5, C: 4.5–5.5 |
| 405b SCATTER DIAGRAM OF PARAMETER SETTING CORRESPONDING TO ALL REFERENCES | A: 1.5–2.5, C: 4.5–5.5 | | |

*FIG. 12*

| ITEM | START TIME | END TIME | SENSITIVITY ANALYSIS TIME | PARAMETERS | | | | REFERENCE KF |
|---|---|---|---|---|---|---|---|---|
| | | | | A | B | C | ... | |
| 314c MINIMUM VALUE | 20 | 50 | 30 | 1.5 | 2.5 | 4.0 | ... | 200 OR SMALLER |
| 315c MAXIMUM VALUE | 40 | | | 2.5 | 3.5 | 6.0 | ... | |
| 316c STRIDE | 1 | | — | 0.1 | 0.1 | 0.2 | ... | |

RESETTING INFORMATION
(EXAMPLE OF RESETTING OF SIMULATION #23)

*FIG. 13*

SIMULATION SYSTEM AND SIMULATION METHOD

TECHNICAL FIELD

The present invention relates to a simulation system.

BACKGROUND ART

Simulations using computers have been widely used for the purpose of simulating the behaviors of systems. Normally, the behavior of a system is converted into a mathematical model and the operation of the model is finely adjusted using parameters in order to execute a simulation. If the simulation is actually executed, the simulation is executed a plurality of times while changing initial values and parameters and the results are compared or subjected to statistical processing in many cases.

There have been conventionally proposed methods of searching or optimizing at least either parameters or a model on the basis of the difference between a simulation result and a result of a phenomenon that actually occurred (see, for example, Patent Literature 1, paragraphs [0017] to [0024] and FIG. 2).

PRIOR ART LITERATURE

Patent Literature

Patent Literature 1: JP-2005-534192-A

SUMMARY OF THE INVENTION

Problem to be Solved by the Invention

If a notable phenomenon has occurred to a simulation, for example, it is necessary to address the additional analysis of the reason of the occurrence of the phenomenon, a method of controlling the phenomenon, and the like. However, the abovementioned background art concerning the simulation is simply a technique for improving simulation accuracy on the basis of an actual result and not for supporting the user's positive, additional analysis of the simulation result.

The present invention has been achieved in the light of the abovementioned problems and an object of the present invention is to provide a simulation method for supporting the user's efficient, additional analysis of a simulation if a notable phenomenon has occurred to the simulation.

DETAILED DESCRIPTION OF EMBODIMENTS

To achieve the object, the present invention includes a simulation system for executing a simulation using a plurality of parameters, including: a processor; and a memory, wherein the memory holds a first evaluation function for executing the simulation by calculating an evaluation value using a first parameter having a plurality of values and at least one second parameter having a plurality of values, and the processor is adapted to: accept information for identifying the plurality of values of the first parameter and the plurality of values of the second parameter; execute a first simulation by calculating a plurality of evaluation values corresponding to the plurality of values of the first parameter using the plurality of values of the second parameter and the first evaluation function; acquire a result group including a plurality of evaluation values to which a predetermined phenomenon occurs from the plurality of evaluation values calculated by the first simulation; acquire a start value and an end value of the first parameter for analyzing the predetermined phenomenon on the basis of the acquired result group; execute a second simulation by calculating a plurality of evaluation values corresponding to the plurality of values of the first parameter from the acquired start value to the acquired end value using the plurality of values of the second parameter and the first evaluation function; and output data for displaying the plurality of evaluation values calculated by the second simulation in such a manner as to be continuous with the evaluation values in the acquired result group corresponding to the acquired start value.

Advantage of the Invention

According to the present invention, the user's efficient, additional simulation analysis is supported.

Objects other than the abovementioned object, configurations, and advantages will be readily apparent from the description of embodiments given below.

BRIEF DESCRIPTION OF THE DRAWINGS

FIG. 12 is an explanatory diagram showing a screen output by a result providing unit according to the third embodiment.

FIG. 13 is an explanatory diagram showing resetting information according to a fourth embodiment.

MODE FOR CARRYING OUT THE INVENTION

Embodiments will now be described hereinafter with reference to the drawings.

First Embodiment

In a first embodiment, a method of supporting an additional simulation analysis by providing a cause of the occurrence of a notable phenomenon and parameters or parameter values capable of controlling the phenomenon if the phenomenon has occurred to a simulation.

Figure 1:
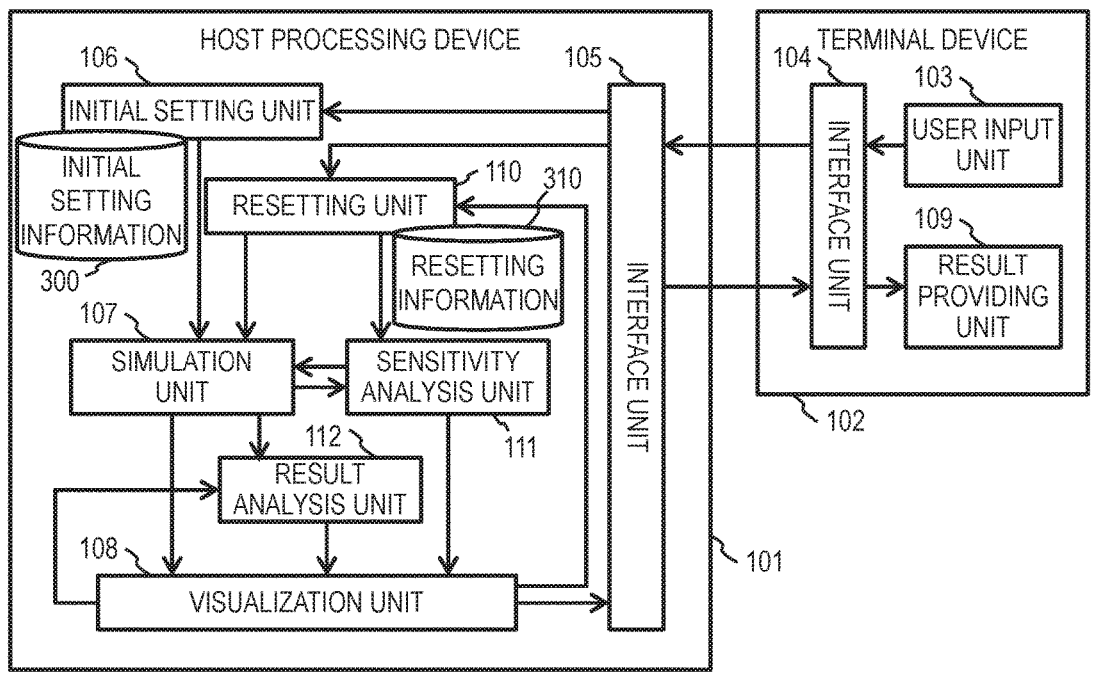
FIG. 1 is a functional block diagram showing a simulation system according to a first embodiment.

FIG. 1 is a functional block diagram showing a simulation system according to the first embodiment.

The simulation system according to the first embodiment includes a host processing device 101 and a terminal device 102. The terminal device 102 includes, as functional units, a user input unit 103, an interface unit 104, and a result providing unit 109.

Furthermore, the host processing device 101 includes, as functional units, an interface unit 105, an initial setting unit 106, a simulation unit 107, a visualization unit 108, a resetting unit 110, a sensitivity analysis unit 111, and a result analysis unit 112. The host processing device 101 includes a storage unit for initial setting information 300 and resetting information 310.

The terminal device 102 is a device for accepting an input by a user and outputting data to the user. The user in the present embodiment means a person who executes a simulation and acquires a result of the simulation. In addition, an administrator according to the present embodiment means a person who administrates or operates the simulation system.

The user input unit 103 is the functional unit that accepts parameters input by the user and a simulation start request instructed by the user.

The result providing unit 109 is the functional unit that outputs the result of the simulation. The interface unit 104 is an interface for communicating with the host processing device 101.

The host processing device 101 is a device for executing the simulation. The interface unit 105 is an interface for communicating with the terminal device 102.

The initial setting unit 106 accepts parameters in a simulation for verifying whether a notable phenomenon occurs. The resetting unit 110 accepts parameters in a simulation for analyzing the notable phenomenon.

The simulation unit 107 functions to perform a simulation using the parameters set by the initial setting unit 106 or the resetting unit 110 and a simulation method (for example, a numerical formula) held in advance.

The result analysis unit 112 functions to determine whether the result of the simulation falls in a preset reference range. The sensitivity analysis unit 111 functions to analyze a parameter having a large influence on the result of the simulation.

The visualization unit 108 functions to generate data for providing the user with the result of the simulation by the simulation unit 107, an analysis result by the result analysis unit 112, and an analysis result by the sensitivity analysis unit 111.

The initial setting information 300 holds information on the parameters used in the simulation for verifying whether a notable phenomenon occurs. The resetting information 310 holds information on the parameters used in the simulation for analyzing the notable phenomenon.

The functional units shown in FIG. 1 may be implemented by a program or may be implemented by different physical devices. Alternatively, a plurality of functional units may be implemented by one program or by one physical device, or one functional unit may be implemented by a plurality of programs or by a plurality of physical devices.

Figure 2:
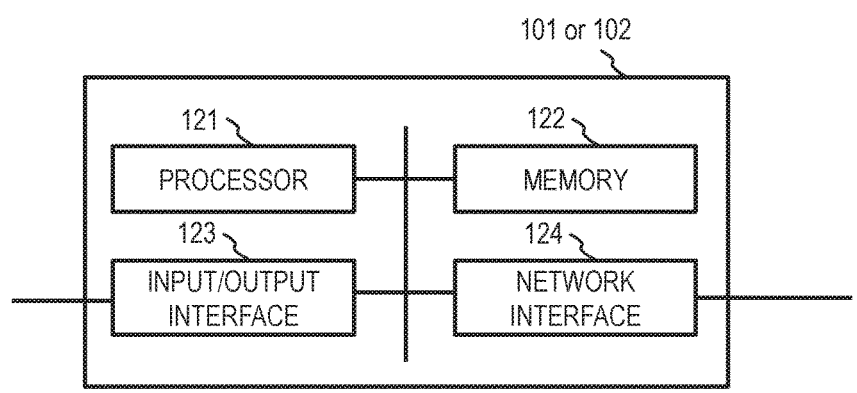
FIG. 2 is a block diagram showing a hardware configuration of each of a host processing device and a terminal device according to the first embodiment.

FIG. 2 is a block diagram showing a hardware configuration of each of the host processing device 101 and the terminal device 102 according to the first embodiment.

Each of the host processing device 101 and the terminal device 102 is a computer and includes a processor 121, a memory 122, and a network interface 124. Furthermore, the terminal device 102 includes an input/output interface 123. Likewise, the host processing device 101 includes the input/output interface 123 if being connected to an output device such as a display or a printer.

The processor 121 is, for example, a CPU and serves as an arithmetic unit and a control unit. The memory 122 is a storage device that retains data. The processor 121 implements the functions of the terminal device 102 or the host processing device 101 by executing a program using the memory 122.

The network interface 124 is a network interface for transmitting and receiving data. The input/output interface 123 is an interface for connecting to the output device such as the display or the printer and to a keyboard, a mouse, and a touch panel.

While the host processing device 101 and the terminal device 102 are implemented by physically different devices in the following description, the host processing device 101 and the terminal device 102 may be implemented by one physical device. Alternatively, the host processing device 101 and the terminal device 102 may be implemented by three or more different devices as long as the functions of the host processing device 101 and the terminal device 102 can be executed.

Figures 3, 4:
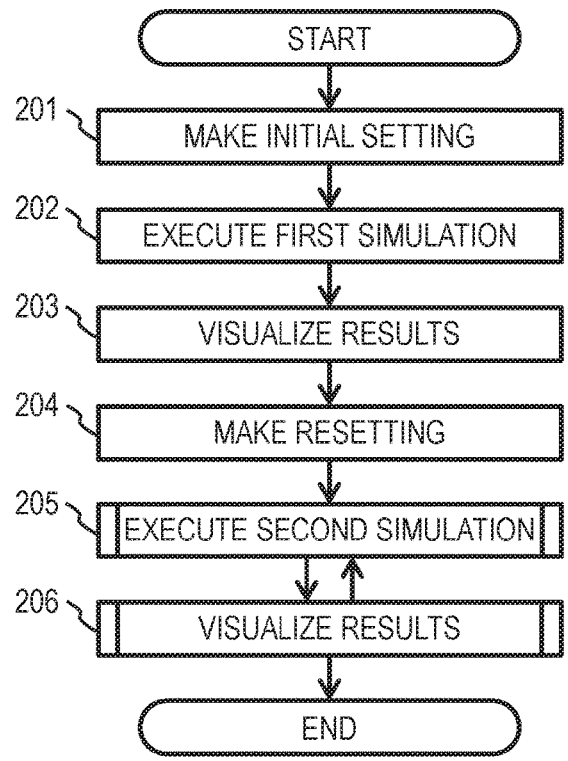
FIG. 3 is a flowchart showing processing performed by the simulation system according to the first embodiment.
FIG. 4 is an explanatory diagram showing initial setting information according to the first embodiment.

FIG. 3 is a flowchart showing processing performed by the simulation system according to the first embodiment.

First, the initial setting unit 106 accepts initial values of the parameters or the like used in a simulation and sets the initial values to the host processing device 101 (201). Specifically, in Step 201, the user input unit 103 accepts initial setting information including the initial values.

The user input unit 103 transmits the accepted initial setting information to the initial setting unit 106 via the interface unit 104 and the interface unit 105. Furthermore, the initial setting unit 106 stores the initial setting information which has received in Step 201 in the storage device such as the memory 122 of the host processing device 101 as the initial setting information 300 necessary for the simulation.

FIG. 4 is an explanatory diagram showing the initial setting information 300 according to the first embodiment.

The initial setting information 300 shown in FIG. 4 is an example. The initial setting information 300 includes arguments of an evaluation function used by the simulation unit 107 in the simulation.

The initial setting information 300 shown in FIG. 4 includes, as items, start time 301, end time 302, and parameters 303. Furthermore, the initial setting information 300 includes, as values of the start time 301, the end time 302, and the parameters 303, minimum values 304, maximum values 305, and strides 306.

The start time 301 is first time of time elapsed in the simulation and time in an initial state in the simulation. The end time 302 is end time of the time elapsed in the simulation. The parameters 303 indicate ranges of values of the arguments of the evaluation function and indicate a plurality of values of at least one argument.

The minimum values 304 and the maximum values 305 each indicate a minimum value or a maximum value of each of the items including the start time 301, the end time 302, and the parameters 303, and each indicate a range of a value that each item can have. The strides 306 each indicate a variation in the values of each item in a combination of the values of the item.

For example, according to the initial setting information 300 shown in FIG. 4, since the maximum value 305 of a parameter A is 5, the minimum value 304 thereof is −5, and the stride 306 thereof is 1, the parameter A is any one of 11 values including −5, −4, −3, −2, −1, 0, 1, 2, 3, 4, and 5. Furthermore, according to the initial setting information 300 shown in FIG. 4, the simulation unit 107 executes a simulation for every time from time 0 to time 100.

Moreover, if the evaluation function used in the simulation is a function for calculating sales in retailing, the parameters include a weather, a date, a day of week, and advertisement fee.

Note that the initial setting information 300 may include any item as long as the values of the arguments used in the simulation can be held. For example, if the arguments of the evaluation function used in the simulation do not include parameters of time, the initial setting information 300 may include a start value and an end value as an alternative for the start time 301 and the end time 302.

After Step 201, the simulation unit 107 acquires the initial setting information 300 from the storage device such as the memory 122, and generates a combination of the values of the parameters 303. The simulation unit 107 performs the simulation using the start time 301, the end time 302, the generated combination, and the evaluation function held in advance (202).

Specifically, the simulation unit 107 executes the simulation by calculating the evaluation function using the generated combination at a plurality of time points indicated by the stride 306 of the start time 301 and the end time 302 between the start time 301 and the end time 302.

Note that the simulation executed in Step 202 will be referred to as first simulation, hereinafter. The first simulation is the simulation for verifying whether a notable phenomenon occurs. Furthermore, the first simulation includes at least one simulation by at least one combination of the values of the parameters.

The notable phenomenon in the first embodiment means a phenomenon that simulation results, that is, evaluation values output in the simulation differ from evaluation values that have been predicted or expected by the user. The user may determine, as the notable phenomenon, the simulation in which an average evaluation value is not output at the end time 302 or may determine, as the notable phenomenon, the simulation in which an average evaluation value is output at the end time 302 but a peculiar evaluation value is output at time other than the end time 302.

In Step 202, the simulation unit 107 outputs a plurality of evaluation values per simulation. To execute the simulation using a plurality of combinations of the values of the parameters 303, a plurality of evaluation values as a plurality of groups is output by a plurality of simulations.

The groups generated by dividing a plurality of evaluation values output when simulations have been executed for every combination of the used values of the parameters 303 will be referred to as result groups, hereinafter.

The simulation unit 107 stores a plurality of generated result groups and the combinations of the values of the parameters 303 corresponding to the result groups in at least one of the storage device, such as the memory 122, included in the host processing device 101 and an external storage device connected to the host processing device 101.

After Step 202, the visualization unit 108 acquires a plurality of evaluation values in the first simulation via the storage device such as the memory 122, and generates image data to be output by the result providing unit 109 on the basis of the acquired evaluation values (203).

Figure 5:
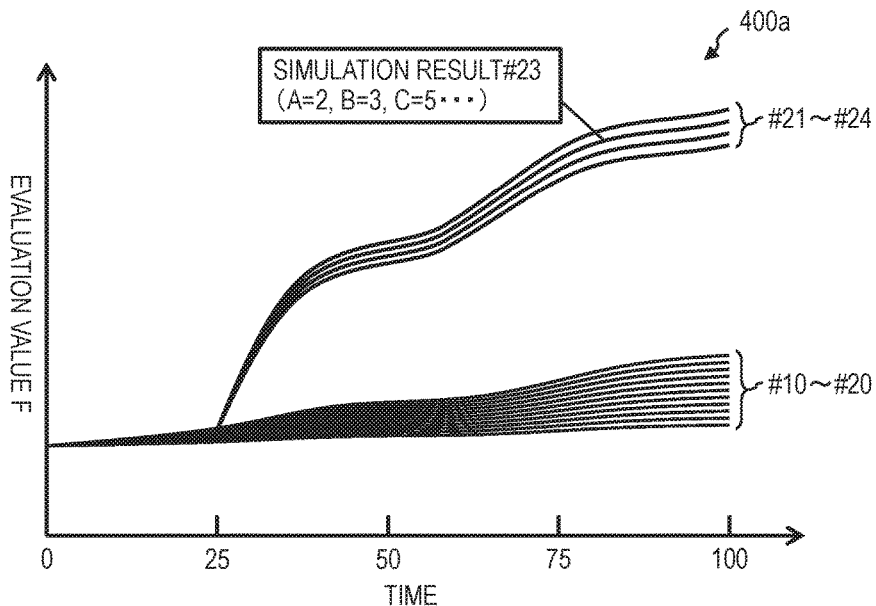
FIG. 5 is an explanatory diagram showing a time series graph displaying a plurality of evaluation values of a first simulation according to the first embodiment.

FIG. 5 is an explanatory diagram showing a time series graph 400a displaying a plurality of evaluation values in the first simulation according to the first embodiment.

The time series graph 400a shown in FIG. 5 is on a screen displayed on the display or the like by the result providing unit 109 on the basis of the image data generated by the visualization unit 108. The time series graph 400a shown in FIG. 5 indicates a plurality of result groups (result groups #10 to #24) generated in the first simulation.

The result groups (result groups #10 to #24) in the first simulation are a set of evaluation values F that have been calculated on the basis of the initial setting information 300 shown in FIG. 4 and the evaluation function. In the time series graph 400a shown in FIG. 5, a horizontal axis indicates the time and a vertical axis indicates the evaluation value F.

The visualization unit 108 generates, in Step 203, the image data for displaying, as the time series graph 400a, the evaluation values F in one simulation that has been executed using one combination of the parameters 303 and the evaluation function.

The result providing unit 109 receives the image data from the visualization unit 108 via the interface units 105 and 104 and outputs the received image data to the user. If the user puts a cursor on a ridge line corresponding to one result group in one simulation, the result providing unit 109 may display identifiers or the used values of the parameters 303 of the result group indicated by the cursor by pop-up.

While the result groups #10 to #20 are constant in increasing tendency, the result groups #21 to #24 remarkably increase at and after time "25." Furthermore, the evaluation values F of the result groups #21 to #24 at end time "100" greatly differ from the evaluation values F of the result groups #10 to #20 at the end time "100."

After Step 203, it is highly likely that the user determines that a notable phenomenon has occurred to a part of the first simulation if reference is made to the evaluation values in the first simulation shown in FIG. 5 and the user has predicted or expected the result groups #10 to #20 as the evaluation values in the first simulation.

If the user instructs the user input unit 103 to execute a re-simulation for analyzing the notable phenomenon, the user input unit 103 accepts resetting information input from the user. The re-simulation for analyzing the notable phenomenon will be referred to as a second simulation, hereinafter. At this time, the user selects one result group in the first simulation to be analyzed by the second simulation from among the result groups #10 to #24 shown in FIG. 5.

The first simulation for the selected result group will be referred to as the analysis simulation, hereinafter. The user inputs, as resetting information, the identifiers of the selected result group (that is, identifiers of the analysis simulation) and parameters and the like used in the second simulation to the user input unit 103.

The user input unit 103 transmits the accepted resetting information to the resetting unit 110 via the interface units 104 and 105. The resetting unit 110 stores the received resetting information in the storage device such as the memory 122 as resetting information 310a necessary for the second simulation (204).

Figure 6:
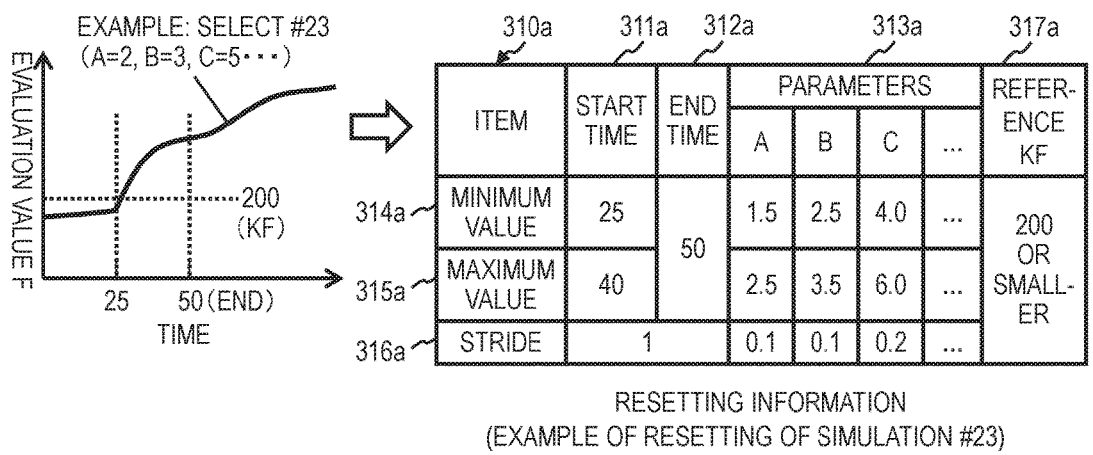
FIG. 6 is an explanatory diagram showing resetting information according to the first embodiment.

FIG. 6 is an explanatory diagram showing the resetting information 310a according to the first embodiment.

The resetting information 310a shown in FIG. 6 indicates a combination of changed values of the parameters and the like when the values of the parameters used in the analysis simulation for the result group #23 are changed halfway along the analysis simulation for the result group #23.

The result group #23 is a set of a plurality of evaluation values in the simulation using a combination of the values of the parameters 303 (A=2, B=3, C=5, . . . ), that is, a set of the evaluation values in the simulation from the start time "0" to the end time "100."

By designating the analysis simulation, the user designates a combination of the values of the parameters 303 used in the simulation to which the notable phenomenon occurs.

The user inputs, as the resetting information, the identifiers of the analysis simulation (that is, identifiers of the combination of the values of the parameters 303) and start time 311a, end time 312a, and values of parameters 313a and a reference 317a shown in FIG. 6. Minimum values 314a, maximum values 315a, and strides 316a are designated to the start time 311a, the end time 312a, and the parameters 313a.

The start time 311a indicates time at which the values of the parameters used to execute the second simulation are changed out of time of outputting the analysis simulation. Owing to this, the start time 311a indicates the time of starting the second simulation.

The end time 312a indicates time of ending the second simulation. The reference 317a is a range of predicted values or expected values of the evaluation values in the second simulation at the end time 312a.

A controllable simulation in the first embodiment means herein a simulation for outputting the evaluation values falling in the range of the reference 317a at the end time 312a. According to FIG. 6, the simulation for which the evaluation values are equal to or smaller than 200 when the time is time "50" is a controllable simulation.

Furthermore, if the evaluation values satisfying the reference 317a at the end time 312a are obtained in the simulation, it means that the simulation unit 107 have been able to control the phenomenon in the simulation.

Time at which it is predicted that the simulation can be controlled by changing the values of the parameters at the start time 311a is designated as the start time 311a. Owing to this, the user may designate time before or after the occurrence of the notable phenomenon as the start time 311a.

The time between the minimum value 314a and the maximum value 315a (time between time "25" and time "40") is designated to the start time 311a of FIG. 6. This indicates that the second simulation using a plurality of combinations of the values of the parameters starts at a plurality of time points between the minimum value and the maximum value.

The parameters 313a indicate ranges of values of arguments of an evaluation function in the second simulation. The values of the parameters 313a may be set again in Step 204 or may be the same as those of the parameters 303 set in Step 201.

The reason for designating the minimum value 314a and the maximum value 315a to the start time of the second simulation is to provide information for identifying the start time at which the evaluation values F can be controlled by performing the simulation a plurality of times from a plurality of start time by the simulation unit 107. As the value of the reference 317a, the range of the evaluation values F predicted to have reached at the end time 312a if no notable phenomenon occurs.

Note that the resetting information 310a may include any items as long as the values of the arguments used in the simulation can be held similarly to the initial setting information 300. For example, if the arguments of the evaluation function used in the simulation do not include parameters of time, the resetting information 310a may include a start value and an end value as an alternative for the start time 311a and the end time 312a.

After Step 204, the simulation unit 107 acquires the resetting information 310a via the storage device such as the memory 122, and executes the simulation using the evaluation values F at the start time 311a of the analysis simulation, the evaluation function held in advance, and the resetting information 310a (205).

The simulation in Step 205 is the second simulation. The second simulation will be described in detail below.

Figure 7:
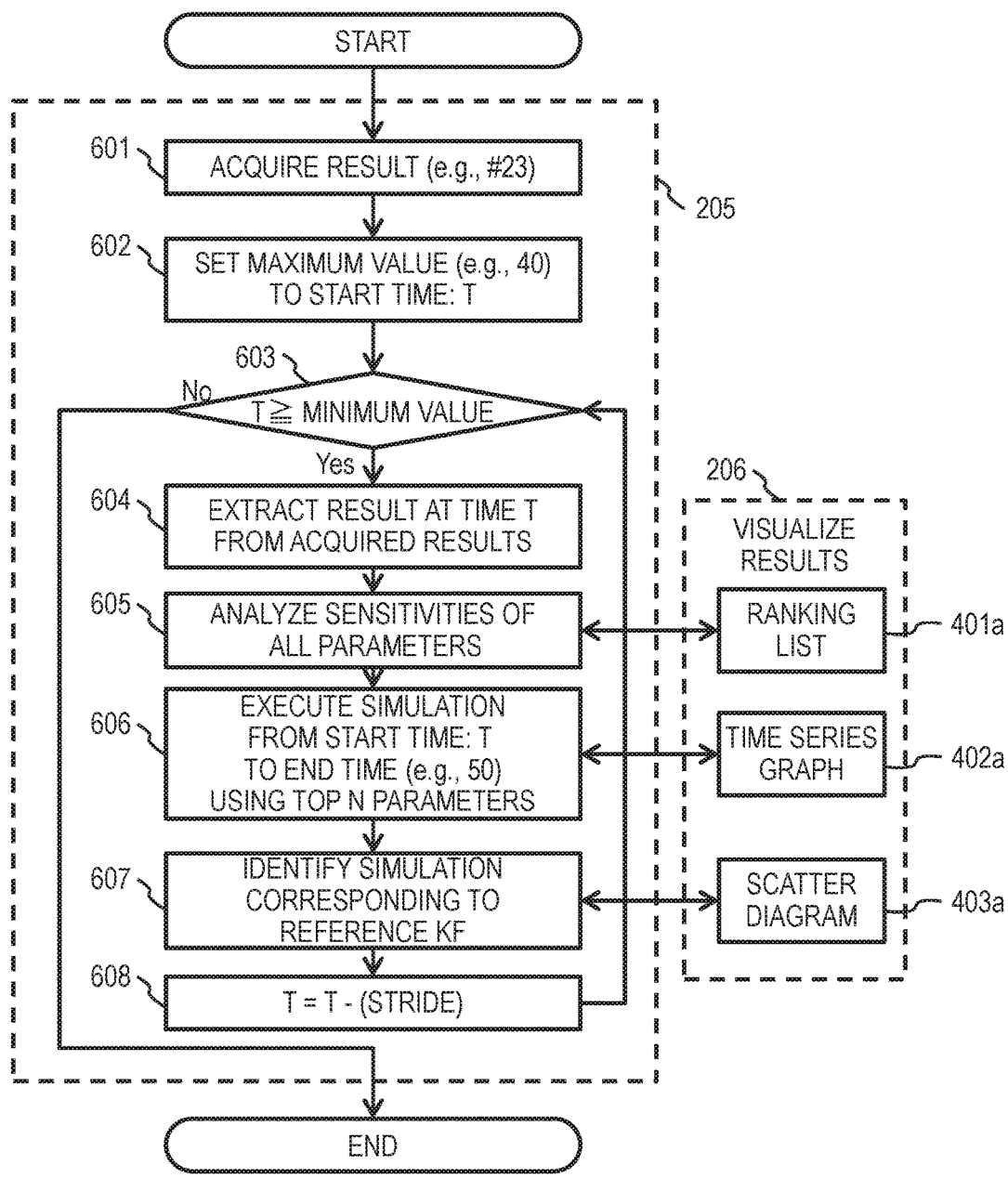
FIG. 7 is a flowchart showing a second simulation and result visualization processing according to the first embodiment.

FIG. 7 is a flowchart showing the second simulation and result visualization processing according to the first embodiment.

In Step 205, the simulation unit 107 first acquires a combination of the values of the parameters 303 in the analysis simulation and the evaluation values output in the second simulation on the basis of the identifiers of the analysis simulation indicated by the resetting information 310a, from the storage device such as the memory 122 (601).

For example, if the analysis simulation indicated by the resetting information 310a is the result group #23, the simulation unit 107 acquires a combination of the parameters 303 (A=2, B=3, C=5 . . . ) and a plurality of evaluation values corresponding to the identifier "#23" from the memory 122 or the like.

After Step 601, the simulation unit 107 acquires the value of the maximum value 315a of the start time 311a from the resetting information 310a and sets the acquired value of the maximum value 315a as the start time T of the second simulation (602). Since the maximum value 315a shown in FIG. 6 is time "40," "40" is set to the start time T of the second simulation.

After Step 602, the simulation unit 107 determines whether the start time T is equal to or greater than the value of the minimum value 314a of the start time 311a in the resetting information 310a (603). This is intended to start the second simulation at a plurality of time included in time between the maximum value 315a and the minimum value 314a of the start time 311a.

If the start time T is equal to or greater than the minimum value 314a of the start time 311a, the simulation unit 107 continues the second simulation. The simulation unit 107 then extracts the evaluation values F at the start time T of the analysis simulation from the evaluation values acquired in Step 601 (604).

The reasons are as follows. The simulation unit 107 executes the second simulation using a plurality of combinations of the values of the parameters 313a at the user's selected start time T of the simulation. Furthermore, the simulation unit 107 extracts initial values of the evaluation function in the second simulation.

After Step 604, the sensitivity analysis unit 111 and the simulation unit 107 analyze the sensitivity of each of the parameters using the evaluation values extracted by the simulation unit 107 as the initial values (605). The sensitivity means herein a ratio of a change in the evaluation values of the simulation to a change in each parameter, and a high sensitivity means herein that an amount of the change in the evaluation values of the simulation with respect to the change in the parameter is greater than those for the other parameters.

Specifically, if the sensitivity analysis unit 111 instructs one parameter the value of which has been changed slightly to the simulation unit 107, the simulation unit 107 executes the simulation using the one parameter the value of which has been changed slightly and the other parameters the values of which have not changed since the start time T as well as the evaluation function.

Changing the value slightly refers herein to change by a value that is sufficiently small compared with the values in the range between the minimum value 314a and the maximum value 315a of each parameter and means, for example, increasing the value by as much as the stride 316a. Furthermore, the administrator of the simulation system according to the first embodiment may instruct a method of changing the parameters at the time of sensitivity analysis to the sensitivity analysis unit 111 in advance.

The sensitivity analysis unit 111 changes the value of each parameter in the simulation and then determines the variation in the evaluation values F for every parameter, thereby analyzing the sensitivity.

For example, the sensitivity analysis unit 111 holds, as a method of analyzing the sensitivity, a method of adding the value of the stride 316a×1 to each parameter. The parameter A corresponding to the result group #23 in the analysis simulation is 2.

In this case, the sensitivity analysis unit 111 instructs, as the parameter A, 2.1 to the simulation unit 107, and the simulation unit 107 executes the simulation from the start time T=40 to the end time 312a using the changed parameter A and the values of the other parameters in the result group #23.

If the evaluation values F are 300 at the start time T=40 and 315 at the end time 312a in this simulation result, the sensitivity analysis unit 111 calculates {(315−300)/300}/0.1=+0.50 as the sensitivity of the parameter A. The sensitivity analysis unit 111 calculates the sensitivities of the other parameters by the same processing.

The sensitivity analysis unit 111 notifies the visualization unit 108 of the calculated sensitivities, and the visualization unit 108 generates image data for displaying ranking lists 401a on the basis of the notified sensitivities (206). The visualization unit 108 generates the image data on the ranking lists 401a where, for example, the parameters are listed in the descending order of sensitivity.

Subsequently, the visualization unit 108 transmits the image data on the ranking lists 401a to the result providing unit 109 via the interface units 104 and 105, and the result providing unit 109 provides the user with the ranking lists 401a at the start time T on the basis of the received image data. Furthermore, the visualization unit 108 transfers the ranking lists 401a to the resetting unit 110.

The subsequent processing is processing for searching conditions for the parameters and the like to control the simulation.

First, the resetting unit 110 extracts top N parameters having the higher sensitivities on the basis of a result of the ranking lists 401a, and stores the extracted parameters in the storage device such as the memory 122 as information necessary for the second simulation to be executed next.

The reason that the resetting unit 110 extracts the N parameters on the basis of the sensitivities is as follows. It is possible to efficiently determine the conditions for making the second simulation controllable with a smaller calculation volume if the simulation is executed with a priority given to the parameters having the higher sensitivities. The conditions for making the second simulation controllable include the values of the parameters and the values of the start time T capable of controlling the simulation.

Owing to this, if the analysis with higher accuracy is desired despite the increased calculation volume, the resetting unit 110 may omit the extraction of the parameters based on the sensitivities.

Note that the value N is a natural number, for example, 2 and may be arbitrarily set in advance by the administrator or the user. Moreover, the user may designate the value N to the resetting unit 110 via the user input unit 103 as a result of referring to the ranking lists 401a.

Furthermore, the functional unit such as the resetting unit 110 may set the value N depending on the result of the sensitivity analysis and the total number of the parameters. For example, the functional unit such as the resetting unit 110 may set one-third of the total number of the parameters as the value N or the number of the parameters for which the result of the sensitivity analysis indicates that the sensitivities are higher than an average value or a central value as the value N.

The simulation unit 107 acquires the abovementioned N parameters from the storage device such as the memory 122. The simulation unit 107 generates a plurality of combinations in which only the values of the N parameters are changed while the values of the other parameters are the same as those of the parameters corresponding to the analysis simulation, on the basis of the resetting information 310.

The simulation unit 107 executes the simulation a plurality of times from the start time T of the analysis simulation to the time of the end time 312a using the generated combinations and the evaluation function (606). The simulation executed in Step 606 is the second simulation.

More specifically, in Step 606, the simulation unit 107 executes the second simulation from the start time T to the end time 312a using the evaluation values calculated in the analysis simulation, the generated combinations, and the evaluation function. If the evaluation function for the simulation is, for example, a function using previous parameters, the simulation unit 107 may use the parameters 313 in the analysis simulation for the second simulation.

In this case, the simulation unit 107 calculates the evaluation values in the second simulation with the evaluation values at the start time T that are initial values calculated at the start time T assumed as the initial values. Specifically, the simulation unit 107 may convert the evaluation function used in the simulation so that the evaluation values calculated at the start time T of the second simulation become equal to the evaluation values calculated at the start time T of the analysis simulation.

By doing so, the simulation unit 107 can change the parameters 313 to be used halfway along the time course of the analysis simulation and execute a plurality of simulations.

In Step 206, the simulation unit 107 transmits a plurality of result groups output by the second simulation to the visualization unit 108 after executing the second simulation, and the visualization unit 108 generates screen data on the time series graph 402a for displaying the result groups similarly to Step 203.

In this case, the visualization unit 108 generates image data on the time series graph 402a such that the result groups in the analysis simulation are continuous with a plurality of result groups in the second simulation. As a result, it is possible to allow the user to compare the result of the first simulation with the result of the second simulation.

In Step 206, the visualization unit 108 transmits the image data on the time series graph 402a to the result providing unit 109 via the interface units 104 and 105. The result providing unit 109 outputs the time series graph 402a at the start time T on the basis of the transmitted image data. Furthermore, the visualization unit 108 transfers the result groups output in the second simulation to the result analysis unit 112 in Step 206.

If a plurality of result groups is transferred from the visualization unit 108 to the result analysis unit 112, the result analysis unit 112 identifies the result group in which the evaluation values F at the end time 312a correspond to the reference 317a from the result groups in the second simulation. The result analysis unit 112 acquires a combination of the values of the parameters used to execute a simulation of the identified result group (607).

For example, the result analysis unit 112 identifies the result group in which the evaluation values F at the end time 312a "50" are equal to or smaller than 200 set as the reference 317a from the execution result of the second simulation, and acquires a combination of the values of the parameters used to execute the simulation of the identified result group.

Furthermore, in Step 607, the result analysis unit 112 notifies the visualization unit 108 of the acquired combination of the values of the parameters. If the result analysis unit 112 is unable to acquire the combination of the values of the parameters in Step 607, the result analysis unit 112 notifies the visualization unit 108 that the result analysis unit 112 has not been able to acquire the combination.

If having been notified by the result analysis unit 112 of the combination of the values of the parameters in the second simulation, the visualization unit 108 generates image data for displaying the notified combination of the values of the parameters as a scatter diagram 403a (206). The visualization unit 108 transmits the image data on the scatter diagram 403a to the result providing unit 109 via the interface units 104 and 105. The result providing unit 109 outputs the scatter diagram 403a at the start time T to the user on the basis of the transmitted image data.

By outputting the scatter diagram 403a, the result providing unit 109 enables the user to recognize the combination of the values of the parameters capable of controlling the simulation to which the notable phenomenon has occurred.

After Step 607, the simulation unit 107 subtracts the value of the stride 316a of the start time 311a from the value of the start time T (608). The simulation unit 107 then executes Step 603. In this way, the host processing device 101 repeats Steps 603 to 608 until the start time T becomes smaller than the minimum value 314a of the start time 311a.

Figures 8, 9:
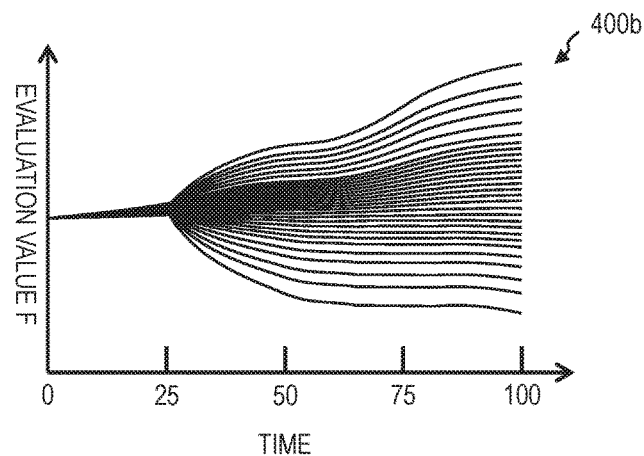
FIG. 8 is an explanatory diagram showing a screen output by a result providing unit according to the first embodiment.
FIG. 9 is an explanatory diagram showing a time series graph displaying a plurality of results of the first simulation according to a second embodiment.

FIG. 8 is an explanatory diagram showing the screen output by the result providing unit 109 according to the first embodiment.

The result providing unit 109 outputs a plurality of ranking lists 401a, a plurality of time series graphs 402a, and a plurality of scatter diagrams 403a at a plurality of start time T. The result providing unit 109 may output the ranking lists 401a, the time series graphs 402a, and the scatter diagrams 403a in such a manner as to be displayed on one screen or to be sequentially displayed.

FIG. 8 shows the ranking lists 401a, the time series graphs 402a, and the scatter diagrams 403a at the start time T of "40," "35," and "30," respectively. Note, however, that if the second simulation has been executed using the resetting information 310a shown in FIG. 6, the start time T has 16 values from 25 to 40 and 16 ranking lists 401a, 16 time series graphs 402a, and the 16 scatter diagrams 403a are, therefore, generated.

According to the ranking lists 401a shown in FIG. 8, the parameters having high sensitivities are parameters A, C, and D at all the start time T. Owing to this, the time series graphs 402a and the scatter diagrams 403a shown in FIG. 8 are the screen generated by the simulation that has been executed by a combination where only the parameters A and C have been changed.

The time series graphs 402a shown in FIG. 8 indicate the result of the second simulation when values of the parameters A and C have been changed. Moreover, the scatter diagrams 403a shown in FIG. 8 indicate the values of the parameters A and C in the simulation of outputting the evaluation values corresponding to the reference 317a by plotting the values with black circles.

According to the time series graphs 402a and the scatter diagrams 403a shown in FIG. 8, if the start time T is "40," the simulation unit 107 is unable to output the evaluation values corresponding to the reference 317a in the second simulation. However, if the start time T is "35" or "30," the simulation unit 107 can output the evaluation values corresponding to the reference 317 in the second simulation by a combination of a part of the parameters.

The user can acquire the combination of the values of the parameters and the start time in the simulation of outputting the evaluation values corresponding to the reference 317a by referring to the screen shown in FIG. 8. In other words, the use can acquire the combination of the values of the parameters and the start time capable of controlling the simulation to output the values in the range of the reference 317a when the notable phenomenon has occurred. The user can thereby analyze the notable phenomenon in more detail.

According to the first embodiment, the ranking lists 401a are output and the result of analyzing the sensitivities is displayed, whereby it is possible to provide the user with the parameters having a large influence on the simulation during the occurrence of the notable phenomenon as an analysis result.

Furthermore, outputting the time series graphs 402a and the scatter diagrams 403a make it possible to indicate whether the notable phenomenon can be controlled. Moreover, in the time series graphs 402a and the scatter diagrams 403a, the combination of the parameters in the simulation of outputting the evaluation values corresponding to the reference 317a and the start time T are displayed, thereby making it possible to provide the user with the start time, the parameters, and the values of the parameters capable of controlling the notable phenomenon as the analysis result.

Owing to this, by outputting at least any of the ranking lists 401a, the time series graphs 402a, and the scatter diagrams 403a, the simulation system according to the first embodiment can provide the user with the information for efficiently and additionally analyzing the result of the simulation.

While in the first embodiment, the set range of the parameters in the simulations is defined by the minimum value, the maximum value, and the stride, the present invention is not limited to the embodiment and the set range of the parameters may be defined by, for example, random variables using an estimated average value and estimated dispersion values.

Furthermore, while in the abovementioned embodiment, the minimum value 314a of the start time T of the second simulation is defined as the time "25" at which the evaluation values F suddenly change (the notable phenomenon occurs), the present invention is not limited to the embodiment and the minimum value 314a of the start time T may be defined as time before or after the time of the occurrence of the notable phenomenon.

Furthermore, if time before the time of the occurrence of the notable phenomenon has been set as the start time T, the visualization unit 108 may extract the parameters having the high sensitivities as the parameters that have caused the occurrence of the notable phenomenon by executing the sensitivity analysis of Step 605 at the start time T. The visualization unit 108 may generate the image data for displaying the parameters that have caused the occurrence of the notable phenomenon.

Moreover, the end time 312*a* of the second simulation may be arbitrarily set as long as the end time 312*a* is the time at which the user desires to obtain the values of the reference 317*a* by the simulation.

Furthermore, while the two axes of the parameters A and C are displayed in the scatter diagrams 403*a* in FIG. 8, the number of axes is not limited to two as that shown in FIG. 8 but one axis or three or more axes may be displayed. Moreover, if the number of axes of the scatter diagrams 403*a* matches the number N of the parameters described above, the user can identify the parameters in the simulation of outputting the evaluation values corresponding to the reference 317*a* from among the changed parameters.

Furthermore, while the visualization unit 108 and the result providing unit 109 output the result of the simulation by a format and an output method of the ranking lists 401*a*, the time series graphs 402*a*, and the scatter diagrams 403*a* shown in FIG. 8, the present invention is not limited to the format and the output method. The visualization unit 108 and the result providing unit 109 may output the result of the simulation by an arbitrary format and an arbitrary output method such as lists, graphs, and tables as long as the user can efficiently perform simulation analysis. Moreover, the result providing unit 109 may display the time series graphs 402*a* and the scatter diagrams 403*a* by, for example, animation according to a change in the start time T.

Furthermore, the strides 316*a* of the parameters in the second simulation may be arbitrary values. Nevertheless, if the strides 316*a* of the parameters 313*a* in the second simulation are smaller than the strides 306 of the parameters 303 in the first simulation, then the exhaustiveness of the simulation can be efficiently enhanced and yet the probability of discovering a phenomenon other than the notable phenomenon can be enhanced.

Moreover, while the time is used as one of the parameters in the abovementioned simulations, any parameters may be used in the simulations according to the first embodiment as long as the parameters are defined as the parameters of the evaluation function.

Second Embodiment

In the first embodiment, the user directly selects the simulation for analyzing the notable phenomenon and directly designates the reference 317*a*. If the notable phenomenon as shown in FIG. 5 occurs, the use can easily recognize the notable phenomenon and can, therefore, make the selection and designation relatively easily.

FIG. 9 is an explanatory diagram showing a time series graph 400*b* displaying a plurality of evaluation values in the first simulation according to a second embodiment.

As indicated by the time series graph 400*b* shown in FIG. 9, for example, if evaluation values that do not fall in a range predicted from evaluation values calculated before the time "25" occurs at the end time after the time "25" but a plurality of result groups is dispersed uniformly, it is difficult for the user to sensuously select the result group to which the notable phenomenon occurs.

To address the problem, according to the second embodiment, a method of providing the user with information capable of positively supporting the selection and designation if it is difficult for the user to select the result of the simulation and to designate the reference 317 will be described.

Configurations of functional units, a storage unit, hardware, and the like according to the second embodiment are the same as those according to the first embodiment. The difference between the second embodiment and the first embodiment is a content of the Step 203.

In Step 203, the visualization unit 108 performs statistical processing on a plurality of results of the simulation in Step 202. Specifically, the visualization unit 108 calculates an average $\mu$ and a standard deviation $\sigma$ with respect to a distribution of a plurality of evaluation values at each time at which the result of the simulation has been obtained. The visualization unit 108 generates image data for displaying results of the average $\mu$ and the standard deviation $\sigma$ as a time series graph 404 as shown in FIG. 10.

Note that the averages $\mu$ and the standard deviations $\sigma$ calculated at the respective time differ, the visualization unit 108 may generate image data for displaying the average $\mu$ and the standard deviation $\sigma$ calculated at the end time 312*a* as the time series graph 404. Furthermore, the visualization unit 108 may generate image data for displaying an average value between each of the average $\mu$ and the standard deviation $\sigma$ calculated at predetermined time before the end time 312*a* and those calculated at the end time 312*a* as the time series graph 404.

Figures 10, 11:
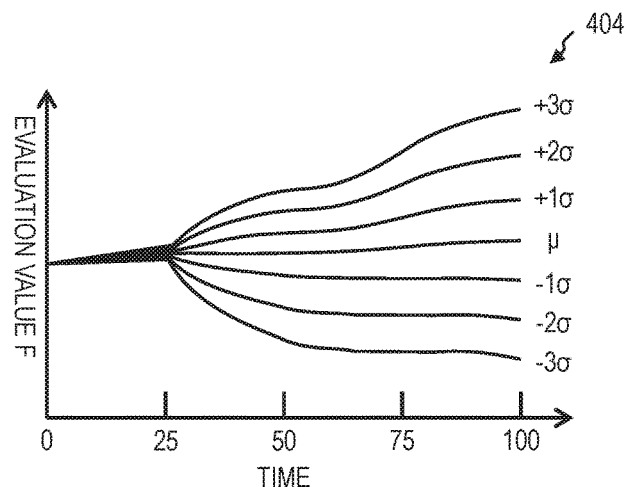
FIG. 10 is an explanatory diagram showing a time series graph displaying standard deviation according to the second embodiment.
FIG. 11 is an explanatory diagram showing resetting information according to a third embodiment.

FIG. 10 is an explanatory diagram showing the time series graph 404 displaying the standard deviation according to the second embodiment.

The visualization unit 108 transmits the image data for displaying the time series graph 400*b* and the image data for displaying the time series graph 404 to the result providing unit 109. The result providing unit 109 displays, for example, the time series graph 400*b* and the time series graph 404 by overlaying one on the other. The result providing unit 109 thereby allows the user to compare the time series graph 400*b* with time series graph 404 to facilitate user's grasping the situation of the dispersion of the result groups.

With this display method, the user can select, as a notable result, the result group, for example, $2\sigma$ or $3\sigma$ closest to the preset standard deviation, and determine the evaluation values F closer to an average $\mu$ as the reference.

The second embodiment exhibits an advantage in that it is possible to output information for positively supporting user's determination for the selection and setting if it is difficult for the user to select the result of the simulation and to set the reference 317, in addition to the advantage of the first embodiment. Therefore, it is possible to support the user's efficient, additional analysis of the result of the simulation.

While the average $\mu$ and the standard deviation $\sigma$ have been employed as indexes for the comparison with the time series graph 400*b* of the result of the simulation in the embodiment, the indexes are not limited thereto and the visualization unit 108 may calculate any indexes as long as the user can easily select the result of the simulation and set the reference.

Third Embodiment

In the first embodiment and the second embodiment, the number of evaluation functions used in the simulations is one and the number of types of the evaluation values F output by the simulations is one. A simulation system according to a third embodiment executes a plurality of simulations using a plurality of evaluation functions while using the same parameters, and changes the parameters halfway along the simulations, thereby providing the user with information for analyzing the notable phenomenon that occurs to each of the simulations.

Furthermore, in the first embodiment and the second embodiment, if the combination of the values of the parameters for controlling one simulation is used in a simulation by the other evaluation function, the user is unable to grasp a change in the simulation by the other evaluation function. To address the problem, the third embodiment provides the result of one simulation by a plurality of evaluation functions when conditions for parameters capable of controlling the simulation by one evaluation function are analyzed.

Configurations of functional units, hardware, and the like according to the third embodiment are the same as those according to the first embodiment. The difference between the third embodiment and the first embodiment is a part of processing in each of Steps 204 to 206.

The simulation unit 107 according to the third embodiment holds a plurality of evaluation functions (evaluation function F, evaluation function G, and evaluation function H) in advance. These evaluation functions use the same types of parameters.

For example, the simulation unit 107 holds the evaluation function F for evaluating the sales of a shop and the evaluation function G for evaluating power consumption cost of the shop. The evaluation functions F and G use the same types of parameters such as the number of customers, a weather of the day, and a temperature.

In Step 202 of the third embodiment, the simulation unit 107 executes a plurality of first simulations using a plurality of evaluation functions. The simulation unit 107 generates a plurality of result groups in a plurality of first simulations.

In Step 203 of the third embodiment, the visualization unit 108 may generate image data on time series graphs 402 for displaying a plurality of result groups in the first simulations, or may generate image data on the time series graphs 402 for displaying a plurality of results in the single first simulation.

Furthermore, in Step 203 of the third embodiment, the user selects the result group to which the notable phenomenon occurs and which is necessary to analyze by referring to a plurality of displayed time series graphs 402. The user thereby selects a combination of the parameters used in the simulation to which the notable phenomenon occurs.

In Step 204, the resetting unit 110 receives resetting information including a plurality of references corresponding to the respective evaluation functions as resetting information 310b. Furthermore, the resetting information 310b includes an identifier of the result selected by the user (for example, result group #23).

FIG. 11 is an explanatory diagram showing the resetting information 310b according to the third embodiment.

Start time 311b, end time 312b, and parameters 313b in the third embodiment are the same as the start time 311a, the end time 312a, and the parameters 313a in the first embodiment. A reference 317b in the third embodiment includes a reference KF, a reference KG, and a reference KH.

The reference KF indicates a range of predicted or expected evaluation values F in the simulation using the evaluation function F. The reference KG indicates a range of predicted or expected evaluation values G in the simulation using the evaluation function G. The reference KH indicates a range of predicted or expected evaluation values H in the simulation using the evaluation function H.

If acquiring the resetting information 310b, the simulation unit 107 of the third embodiment executes the second simulation using a plurality of evaluation functions in Step 205. As a result, a plurality of evaluation values (evaluation values F, evaluation value G, and evaluation value H) is output.

Specifically, the simulation unit 107 extracts the result groups generated using the same parameters as the parameters selected by the user in Step 203 from the result groups in a plurality of first simulations executed by a plurality of evaluation functions in Step 601 of the third embodiment for every evaluation function. The simulation unit 107 acquires contents of the extracted result groups from the storage device such as the memory 122.

Steps 602 and 603 of the third embodiment are the same as Steps 602 and 603 of the first embodiment.

In Step 604 of the third embodiment, the simulation unit 107 extracts the evaluation values at the start time T from the result acquired in Step 601. Note that if a plurality of evaluation functions is three evaluation functions, the number of extracted results is similarly three.

In Step 605 of the third embodiment, the simulation unit 107 and the sensitivity analysis unit 111 analyze the sensitivity of each parameter similarly to the first embodiment. The evaluation function used in this case may be the evaluation function used to generate the result group selected in Step 203 or may be the other evaluation function.

In Step 606 of the third embodiment, the simulation unit 107 executes the second simulation using the respective evaluation functions by changing a combination of the top N parameters from the start time T.

In Step 607 of the third embodiment, the simulation unit 107 identifies the result groups corresponding to the references indicated by the reference 317b from the result groups in the second simulation by a plurality of evaluation functions for every evaluation function. The visualization unit 108 generates image data on scatter diagrams 403b indicating a combination of the parameters 313b used to generate the identified result group for every evaluation function.

In this way, in Step 206 of the third embodiment, the visualization unit 108 generates the image data on a ranking list 401b, the time series graphs 402b, and the scatter diagrams 403b for displaying a plurality of results by a plurality of evaluation functions.

Furthermore, the visualization unit 108 of the third embodiment generates image data on a scatter diagram 405b after Step 607. The scatter diagram 405b displays a combination of parameters that have generated the result groups corresponding to all references indicated by the reference 317b among the combinations of the parameters 313b corresponding to the result groups.

The visualization unit 108 of the third embodiment transmits the generated image data to the result providing unit 109, and the result providing unit 109 displays the ranking list 401b, the time series graphs 402b, the scatter diagrams 403b, and the scatter diagram 405b on the basis of the transmitted image data.

FIG. 12 is an explanatory diagram showing a screen output by the result providing unit 109 according to the third embodiment.

The ranking list 401b of FIG. 12 is the ranking list 401b generated when the user has selected the result (result group #23) of one simulation from the first simulation using the evaluation function F in Step 203. Furthermore, the ranking list 401b is generated when the sensitivity analysis unit 111 and the simulation unit 107 have analyzed the sensitivities using the evaluation function F.

Moreover, the time series graphs 402b, the scatter diagrams 403b, and the start scatter diagram 405b in FIG. 12 are the time series graphs 402b, the scatter diagrams 403b, and the scatter diagram 405b when the values of the parameters A and C have changed at the start time T. The time series graphs 402b shown in FIG. 12 indicate the evaluation values F, the evaluation values G, and the evaluation values H that are the result of the simulations.

The scatter diagrams 403b shown in FIG. 12 indicate combinations of the values of the parameters 313b in the simulations that have output the results corresponding to the reference KH, the reference KG, and the reference KH. Moreover, the scatter diagram 405b shown in FIG. 12 indicates a combination of the values of the parameters 313b in the simulation that has output the result corresponding to each of the reference KH, the reference KG, and the reference KH in all the simulations by the evaluation function F, the evaluation function G, and the evaluation function H.

Note that the screen shown in FIG. 12 indicates a screen when the start time T is 30. Nevertheless, if the resetting information 310b shown in FIG. 11 is used, the start time T has 16 values from 25 to 40; the result providing unit 109, thus, may display all screens at the start time T having these 16 values or display screens at a part of the time.

As described so far, the third embodiment exhibits an advantage in that the user can confirm, by the time series graphs 402b, a behavior as to how the results of a plurality of simulations using a plurality of evaluation functions change if changing the parameters, in addition to the advantages of the first embodiment and the second embodiment. Furthermore, the user can confirm, by the scatter diagram 405b, the values of the parameters 313b that can output the results corresponding to the reference 317b set for a plurality of evaluation functions.

Owing to this, the third embodiment provides a method that enables the user to efficiently and additionally analyze the result of the simulation, which is the object of the present invention, and a system therefor.

Note that while the number of the evaluation functions is three in the abovementioned embodiment, the number of the evaluation functions is not limited to three but the number of the evaluation functions in the third embodiment may be an arbitrary number as long as the number is two or more. Furthermore, while the result providing unit 109 displays the ranking list 401b only for the evaluation function F in FIG. 12, the display of the ranking list 401b is not limited to that for the evaluation function F. Specifically, the sensitivity analysis unit 111 and the simulation unit 107 of the third embodiment may analyze the sensitivities of the parameters 313b using the evaluation functions G and H, and the result providing unit 109 of the third embodiment may display those results as the ranking lists 401b.

Moreover, in Step 203 in the third embodiment, similarly to Step 203 in the second embodiment, the visualization unit 108 may calculate the average $\mu$ and the standard deviation $\sigma$ of the results of the first simulations, and the result providing unit 109 may display the time series graph 404 displaying the average $\mu$ and the standard deviation $\sigma$ for each of a plurality of evaluation functions.

Fourth Embodiment

The sensitivity analysis unit 111 in the first to third embodiments analyzes the sensitivities at the start time T, thereby determining the parameters to be changed in the second simulation. However, if the host processing device 101 sets the start time T before the occurrence of the notable phenomenon (for example, before the time "25" shown in FIG. 6) and analyzes the sensitivities, there is a probability that sudden changes in the evaluation values F after the occurrence of the notable phenomenon are not reflected in the sensitivity analysis. As a result, there is a probability that the simulation unit 107 is unable to correctly use the parameters effective for controlling the sudden changes in the evaluation values F.

In a fourth embodiment, therefore, a method of correctly extracting parameters effective for controlling the notable phenomenon even in the abovementioned case will be described.

Configurations of functional units, hardware, and the like according to the fourth embodiment are the same as those according to the first embodiment. The difference between the fourth embodiment and the first embodiment is a content of the resetting information 310 and a part of processing in each of Steps 204 and 205.

FIG. 13 is an explanatory diagram showing resetting information 310c according to the fourth embodiment.

The resetting information 310c includes start time 311c, end time 312c, parameters 313c, and a reference 317c. Furthermore, the resetting information 310c indicates a minimum value 314c, a maximum value 315c, and a stride 316c of the start time 311c, and the minimum values 314c, the maximum values 315c, and the strides 316c of the parameters 313c.

The resetting information 310c of the fourth embodiment, differently from the resetting information 310a of the first embodiment, includes sensitivity analysis time 318c. The sensitivity analysis time 318c indicates start time of a simulation for executing sensitivity analysis in Step 605. The time indicated by the sensitivity analysis time 318c does not necessarily match the time indicated by the start time 311c.

In Step 203, the user inputs a value of the sensitivity analysis time 318c to the user input unit 103. In this case, the user inputs, as the value of the sensitivity analysis time 318c, time after the occurrence of the notable phenomenon.

As described so far, the simulation analysis method of the fourth embodiment exhibits an advantage in that it is possible to accurately extract the parameters the values of which are changed in the second simulation in order to execute the simulation for the sensitivity analysis from the time that is not associated with the start time of the second simulation, in addition to the advantages of the first to third embodiments. As a result, it is possible to correctly extract the parameters effective for controlling the evaluation values.

Owing to this, the fourth embodiment provides the method that enables the user to efficiently and additionally analyze the result of the simulation, which is the object of the present invention, and a system therefor.

In the fourth embodiment, the user inputs the sensitivity analysis time 318c; alternatively, for example, the visualization unit 108 (or result analysis unit 112 or the like) of the host processing device 101 may calculate a variation per unit time in the evaluation values F as the result of the first simulation and the result providing unit 109 may display the result while overlaying the result on the time series graph 400a. It is thereby possible to positively support the user's determination as to the input of the sensitivity analysis time.

Furthermore, in Step 203 in the fourth embodiment, similarly to Step 203 in the second embodiment, the visualization unit 108 may calculate the average $\mu$ and the standard deviation $\sigma$ of the results of the first simulations, and the result providing unit 109 may display the time series graph 404 displaying the average μ and the standard deviation σ.

Moreover, the simulation unit 107 in the fourth embodiment, similarly to the simulation unit 107 in the third embodiment, may execute a plurality of first simulations by a plurality of evaluation functions. The user then may input the sensitivity analysis time for any of the evaluation functions after referring to the result of the first simulations by a plurality of evaluation functions in Step 203.

Fifth Embodiment

A simulation system of a fifth embodiment combines the methods described in the first, second, and fourth embodiments and determines the values of resetting information 310, thereby automatically executing result analysis by the second simulation.

Figure 14:
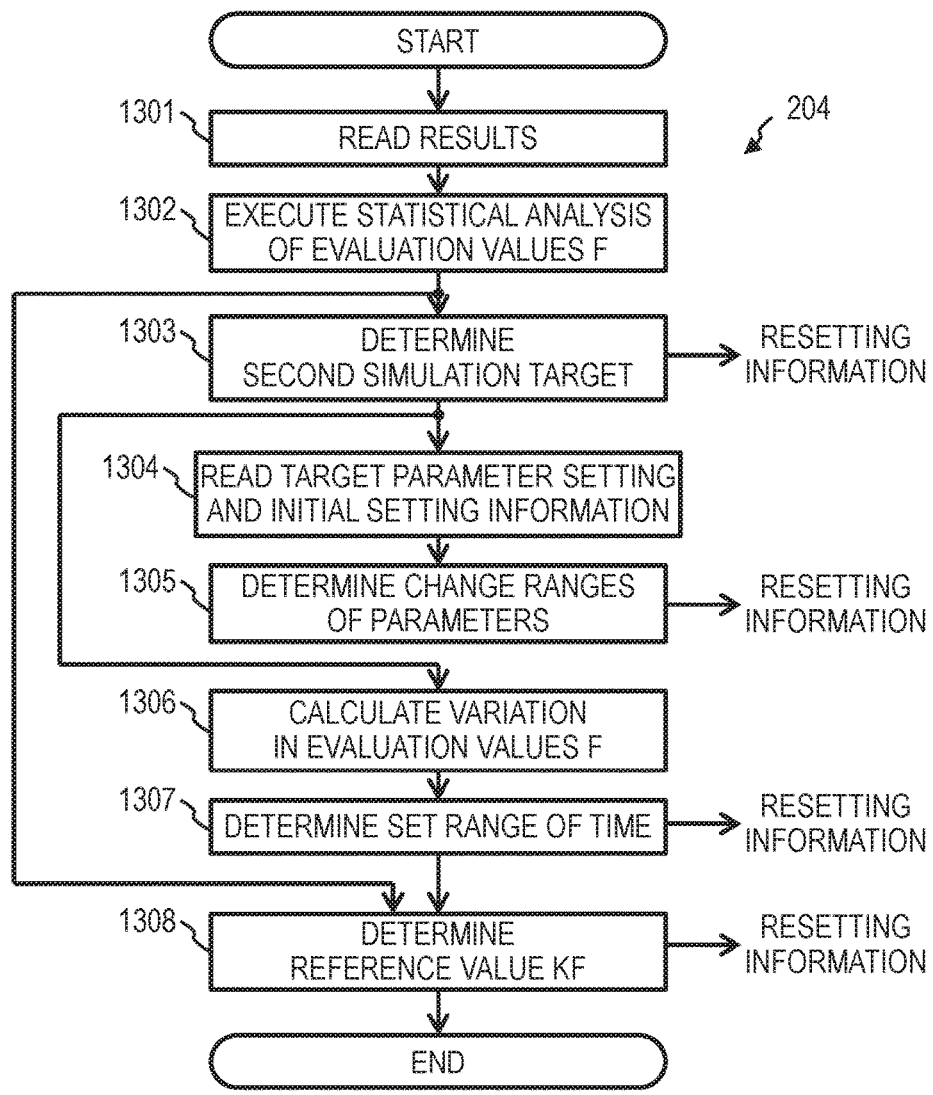
FIG. 14 is a flowchart showing processing performed by a resetting unit according to a fifth embodiment.

FIG. 14 is a flowchart showing processing performed by the resetting unit 110 according to the fifth embodiment.

Configurations of functional units, hardware, and the like according to the fifth embodiment are the same as those according to the first embodiment. The difference between the fifth embodiment and the first embodiment is Step 204. In Step 204 of the fifth embodiment, the user input unit 103 does not accept the resetting information 310 from the user.

On the other hand, in Step 204 of the fifth embodiment, the resetting unit 110 reads all of a plurality of result groups in the first simulation (1301). After Step 1301, the resetting unit 110 performs statistical processing on the evaluation values F in a plurality of read result groups (1302).

After Step 1302, the resetting unit 110 determines the result group (that is, a combination of the simulation unit and the values of the parameters 303) to be analyzed by the second simulation on the basis of a result of the statistical processing (1303).

The statistical processing in Step 1302 may be the same as the statistical processing executed by the visualization unit 108 in the second embodiment. Specifically, the resetting unit 110 calculates the average μ and the standard deviation σ with respect to the distribution of a plurality of evaluation values F at each time at which the result of the simulation has been obtained in Step 1302.

In Step 1303, the resetting unit 110 determines the simulation that has output the result group, for example, 2σ or 3σ closest to the preset standard deviation, as the simulation to which the notable phenomenon has occurred and which is to be analyzed by the second simulation. The resetting unit 110 stores the identifier of the determined simulation in the resetting information 310.

After Step 1303, the resetting unit 110 reads a combination of the values of the parameters 303 used in the determined simulation and the initial setting information 300 from the storage device such as the memory 122 (1304). After Step 1304, the resetting unit 110 determines the ranges of the parameters 313 (1305).

Specifically, the resetting unit 110 sets, for example, the values of the parameters 303 in the simulation determined in Step 1303 as central values. In Step 1305, the resetting unit 110 calculates the ranges of the parameters in the second simulation by multiplying a preset coefficient A (for example, 1/10) by the range (value obtained by subtracting the minimum value 304 from the maximum value 305) of each of the parameters indicated by the parameters 303 in the initial setting information 300. The resetting unit 110 determines the minimum values 314 and the maximum values 315 on the basis of the set central values and the calculated ranges.

Furthermore, in Step 1305, the resetting unit 110 calculates the strides 316 of the parameters in the second simulation by acquiring a preset coefficient B (for example, 1/10) by the stride 306 of each of the parameters 303.

The resetting unit 110 stores the ranges of the parameters 313 determined in Step 1305 in the parameters 313 in the resetting information 310.

After Step 1303 or Step 1305, the resetting unit 110 calculates the variation in the evaluation values F in the simulation determined in Step 1303 (1306). The resetting unit 110 then determines start time 311 and end time 312 on the basis of the analysis result (1307).

Specifically, the resetting unit 110 calculates the variation per unit time in the evaluation values F in the determined simulation in Step 1306. The resetting unit 110 then extracts the time at which the calculated variation is the largest in Step 1307. The resetting unit 110 determines the extracted time as sensitivity analysis time 318, and determines the extracted time as the central value of the start time 311 and the end time 312.

In Step 1307, the resetting unit 110 multiplies a preset coefficient C (for example, 1/10) by the difference between the start time 301 and the end time 302 in the initial setting information 300. The resetting unit 110 determines the start time 311 and the end time 312 so that the value obtained by the multiplication becomes the difference between the start time 311 and the end time 312. Alternatively, the resetting unit 110 may determine the same value as, for example, the stride 306 in the initial setting information 300, as a stride 316 of the start time 311 and the end time 312.

After Step 1302 or Step 1307, the resetting unit 110 determines a reference 317 (1308). Specifically, the resetting unit 110 may determine the reference 317 using, for example, the value of the average μ and the range of the standard deviation σ calculated in Step 1302 at the same time as the end time 312 determined in Step 1307.

The resetting unit 110 stores the information determined in Steps 1307 and 1308 in the storage device such as the memory 122 as the resetting information 310. As a result, the simulation unit 107 can automatically execute the second simulation after the first simulation without accepting the resetting information 310 input from the user. Note that the user input unit 103 may accept the aforementioned coefficients A, B, and C from the user before or during the processing shown in FIG. 14.

As described so far, the fifth embodiment exhibits an advantage in that the resetting information 310 can be set without relying on user's input, in addition to the advantages of the first to the fourth embodiments. It is thereby possible to provide the user with the information for analyzing the notable phenomenon promptly after the execution of the first simulation.

Therefore, it is possible to provide a simulation analysis method that enables the user to efficiently and additionally analyze the result of the simulation, which is the object of the present invention, and a system therefor.

Note that the fifth embodiment may be applied to any of the first to third embodiments.

Furthermore, in the first to fifth embodiments, it is desirable that the sensitivities of the parameters used in the simulation are normalized as much as possible for the evaluation values in a normal state. Here, it is considered that the normal state is a state in which the average value μ shown in, for example, the second embodiment is used.

Furthermore, actual simulations to which the embodiments of the present invention are applicable are not limited to a specific simulation as long as the result of the simulation can be provided in the form of the time series graph 402, and may include an interest rate simulation, a chain-reaction bankruptcy simulation, an evacuation guidance simulation, and a circuit simulation.

Moreover, the present invention is not limited to the aforementioned embodiments and encompasses various modifications. For example, the abovementioned embodiments have been described in detail for describing the present invention so that the present invention is easy to understand. The present invention is not always limited to the embodiments having all the configurations described so far.

Furthermore, the configuration of the certain embodiment can be partially replaced by the configuration of the other embodiment or the configuration of the other embodiment can be added to the configuration of the certain embodiment. Moreover, for a part of the configuration of each embodiment, the other configuration can be added, deleted or replaced.

Furthermore, a part of or all of each of the configurations, the functions, the processing units, processing procedures, and the like described above may be realized by hardware by, for example, designing by an integrated circuit. Moreover, each of the configurations, the functions, and the like described above may be realized by software by interpreting a program for causing a processor to realize the respective functions and executing the functions. Information on a program, a table, a file, and the like for realizing each function may be placed in a recording device such as a memory, a hard disk or an SSD (Solid State Drive), or in a recording medium such as an IC card, an SD card or a DVD.

Furthermore, control lines or information lines considered to be necessary for the description are illustrated and all the control lines or the information lines are not always illustrated in terms of a product. In actuality, it may be assumed that almost all the configurations are mutually connected.

The invention claimed is:

1. A simulation system for executing a simulation using a plurality of parameters, comprising:
   a simulation host processor; and
   a memory coupled to the simulation host processor and storing a first evaluation function for executing the simulation by the simulation host processor by calculating an evaluation value using a first parameter having a plurality of values and at least one second parameter having a plurality of values,
   wherein the simulation host processor is configured to
      accept information for identifying the plurality of values of the first parameter and the plurality of values of the second parameter;
      execute a first simulation by calculating a plurality of evaluation values corresponding to the plurality of values of the first parameter using the plurality of values of the second parameter and the first evaluation function;
      acquire a result group including a plurality of evaluation values to which a predetermined phenomenon occurs from the plurality of evaluation values calculated by the first simulation;
      acquire a start value and an end value of the first parameter for analyzing the predetermined phenomenon on the basis of the acquired result group;
      execute a second simulation by calculating a plurality of evaluation values corresponding to the plurality of values of the first parameter from the acquired start value to the acquired end value using the plurality of values of the second parameter and the first evaluation function;
      output data for displaying the plurality of evaluation values calculated by the second simulation in such a manner as to be continuous with the evaluation values in the acquired result group corresponding to the acquired start value;
      accept information for identifying a plurality of combinations of the values of a plurality of the second parameters;
      execute the first simulation by calculating a plurality of evaluation values corresponding to the plurality of values of the first parameter using the plurality of combinations of the values of the plurality of the second parameters and the first evaluation function;
      acquire a result group including a plurality of evaluation values to which the predetermined phenomenon occurs from the plurality of evaluation values calculated by the first simulation;
      identify a first combination of the values of the second parameters used to calculate the evaluation values included in the acquired result group;
      generate a plurality of second combinations of the values of the second parameters for analyzing a sensitivity of each of the second parameters by changing the respective values of the second parameters included in the identified first combination;
      acquire an analysis value of the first parameter determined to analyze the sensitivity;
      identify the evaluation values in the acquired result group corresponding to the acquired analysis value;
      execute a fifth simulation by calculating a plurality of evaluation values corresponding to the plurality of values of the first parameter using the plurality of second combinations and the first evaluation function;
      calculate a sensitivity indicating a magnitude of an influence of each of the plurality of second parameters on a result of the fifth simulation on the basis of the plurality of evaluation values calculated by the fifth simulation;
      determine at least one second parameter used in the second simulation on the basis of the calculated sensitivity;
      execute the second simulation using the plurality of values of the determined second parameter and the first evaluation function;
      calculate a ratio of a change in the plurality of evaluation values in the acquired result group; and
      acquire the analysis value by determining the value of the first parameter highest in the calculated ratio of the change as the analysis value.

2. The simulation system according to claim 1, wherein the simulation host processor is further configured to
   acquire a first range of the evaluation values calculated by the first evaluation function at the end value;
   extract the evaluation value corresponding to the end value and falling in the first range from the plurality of evaluation values calculated by the second simulation; and
   output, as a first control value, the value of the second parameter used to calculate the extracted evaluation value falling in the first range.

3. The simulation system according to claim 2, wherein the memory holds a second evaluation function other than the first evaluation function and that executes the simulation by calculating evaluation values using the first parameter and the second parameter, and
the simulation host processor is further configured to
acquire a second range of the evaluation values calculated by the second evaluation function at the end value;
identify the values of the second parameter corresponding to the acquired result group;
execute a third simulation by calculating a plurality of evaluation values corresponding to the plurality of values of the first parameter using the identified values of the second parameter and the second evaluation function;
execute a fourth simulation by calculating a plurality of evaluation values corresponding to the plurality of values of the first parameter from the acquired start value to the acquired end value in such a manner as to be continuous with the evaluation values calculated by the third simulation corresponding to the acquired start value using the plurality of values of the second parameter and the second evaluation function;
extract the evaluation value corresponding to the end value and falling in the second range from the plurality of evaluation values calculated by the fourth simulation;
identify, as a second control value, the value of the second parameter used to calculate the extracted evaluation value falling in the second range;
extract, as a third control value, the value of the second parameter that serves as the first control value and the second control value; and
generate data for displaying the extracted third control value.

4. The simulation system according to claim 1, wherein the simulation host processor is further configured to
identify a minimum value of the first parameter; and
acquire the start value by determining, as the start value, a value smaller than the determined analysis value and larger than the minimum value of the first parameter.

5. The simulation system according to claim 1, wherein the simulation host processor is further configured to
hold a predetermined standard deviation of the result group to which the predetermined phenomenon occurs, in the memory;
divide the plurality of evaluation values calculated by the first simulation into result groups corresponding to the respective plurality of values of the second parameter;
calculate a standard deviation of the plurality of evaluation values for every value of the first parameter included in the plurality of result groups; and
acquire the result group for which a standard deviation closest to the predetermined standard deviation has been calculated from the plurality of result groups, as a result group including the plurality of evaluation values to which the predetermined phenomenon occurs.

6. The simulation system according to claim 1, wherein the values of the first parameter are time, and
the simulation host processor is configured to execute the first simulation according to the time using the plurality of values of the second parameter and the first evaluation function.

7. A simulation method performed by a simulation system using a plurality of parameters,
the simulation system including a simulation host processor and a memory,
the memory storing a first evaluation function for executing the simulation by calculating an evaluation value using a first parameter having a plurality of values and at least one second parameter having a plurality of values,
the simulation method comprising:
a step of accepting, by the simulation host processor, information for identifying the plurality of values of the first parameter and the plurality of values of the second parameter;
a step of executing, by the simulation host processor, a first simulation by calculating a plurality of evaluation values corresponding to the plurality of values of the first parameter using the plurality of values of the second parameter and the first evaluation function;
a step of acquiring, by the simulation host processor, a result group including a plurality of evaluation values to which a predetermined phenomenon occurs from the plurality of evaluation values calculated by the first simulation;
a step of acquiring, by the simulation host processor, a start value and an end value of the first parameter for analyzing the predetermined phenomenon on the basis of the acquired result group;
a step of executing, by the simulation host processor, a second simulation by calculating a plurality of evaluation values corresponding to the plurality of values of the first parameter from the acquired start value to the acquired end value using the plurality of values of the second parameter and the first evaluation function;
a step of outputting, by the simulation host processor, data for displaying the plurality of evaluation values calculated by the second simulation in such a manner as to be continuous with the evaluation values in the acquired result group corresponding to the acquired start value;
a step of accepting, by the simulation host processor, information for identifying a plurality of combinations of the values of a plurality of the second parameters;
a step of executing, by the simulation host processor the first simulation by calculating a plurality of evaluation values corresponding to the plurality of values of the first parameter using the plurality of combinations of the values of the plurality of the second parameters and the first evaluation function;
a step of acquiring, by the simulation host processor a result group including a plurality of evaluation values to which the predetermined phenomenon occurs from the plurality of evaluation values calculated by the first simulation;
a step of identifying, by the simulation host processor, a first combination of the values of the second parameters used to calculate the evaluation values included in the acquired result group;
a step of generating, by the simulation host processor a plurality of second combinations of the values of the second parameters for analyzing a sensitivity of each of the second parameters by changing the respective values of the second parameters included in the identified first combination;
a step of acquiring, by the simulation host processor, an analysis value of the first parameter determined to analyze the sensitivity;

a step of identifying, by the simulation host processor, the evaluation values in the acquired result group corresponding to the acquired analysis value;

a step of executing, by the simulation host processor, a fifth simulation by calculating a plurality of evaluation values corresponding to the plurality of values of the first parameter using the plurality of second combinations and the first evaluation function;

a step of calculating, by the simulation host processor, a sensitivity indicating a magnitude of an influence of each of the plurality of second parameters on a result of the fifth simulation on the basis of the plurality of evaluation values calculated by the fifth simulation;

a step of determining, by the simulation host processor, at least one second parameter used in the second simulation on the basis of the calculated sensitivity;

a step of executing, by the simulation host processor, the second simulation using the plurality of values of the determined second parameter and the first evaluation function;

a step of calculating, by the simulation host processor, a ratio of a change in the plurality of evaluation values in the acquired result group; and a step of acquiring, by the simulation host processor, the analysis value by determining the value of the first parameter highest in the calculated ratio of the change as the analysis value.

8. The simulation method according to claim 7, comprising:

a step of acquiring, by the simulation host processor, a first range of the evaluation values calculated by the first evaluation function at the end value;

a step of extracting, by the simulation host processor, the evaluation value corresponding to the end value and falling in the first range from the plurality of evaluation values calculated by the second simulation; and a step of outputting, by the simulation host processor, as a first control value, the value of the second parameter used to calculate the extracted evaluation value falling in the first range.

9. The simulation method according to claim 8, wherein the memory stores a second evaluation function other than the first evaluation function and that executes the simulation by calculating evaluation values using the first parameter and the second parameter, and the method further comprises:

a step of acquiring, by the simulation host processor, a second range of the evaluation values calculated by the second evaluation function at the end value;

a step of identifying, by the simulation host processor, the values of the second parameter corresponding to the acquired result group;

a step of executing, by the simulation host processor, a third simulation by calculating a plurality of evaluation values corresponding to the plurality of values of the first parameter using the identified values of the second parameter and the second evaluation function;

a step of executing, by the simulation host processor, a fourth simulation by calculating a plurality of evaluation values corresponding to the plurality of values of the first parameter from the acquired start value to the acquired end value in such a manner as to be continuous with the evaluation values calculated by the third simulation corresponding to the acquired start value using the plurality of values of the second parameter and the second evaluation function;

a step of extracting, by the simulation host processor, the evaluation value corresponding to the end value and falling in the second range from the plurality of evaluation values calculated by the fourth simulation;

a step of identifying, by the simulation host processor, as a second control value, the value of the second parameter used to calculate the extracted evaluation value falling in the second range;

a step of extracting, by the simulation host processor, as a third control value, the value of the second parameter that serves as the first control value and the second control value; and a step of generating, by the simulation host processor, data for displaying the extracted third control value.

10. The simulation method according to claim 7, comprising:

a step of identifying, by the simulation host processor, a minimum value of the first parameter; and a step of acquiring, by the simulation host processor, the start value by determining, as the start value, a value smaller than the determined analysis value and larger than the minimum value of the first parameter.

11. The simulation method according to claim 7, wherein a predetermined standard deviation of the result group to which the predetermined phenomenon occurs is held in the memory, and the method comprises:

a step of dividing, by the simulation host processor, the plurality of evaluation values calculated by the first simulation into result groups corresponding to the respective plurality of values of the second parameter;

a step of calculating, by the simulation host processor, a standard deviation of the plurality of evaluation values for every value of the first parameter included in the plurality of result groups; and a step of acquiring, by the simulation host processor, the result group for which a standard deviation closest to the predetermined standard deviation has been calculated from the plurality of result groups, as a result group including the plurality of evaluation values to which the predetermined phenomenon occurs.

12. A simulation system for executing a simulation using a plurality of parameters, comprising:

a simulation host processor; and a memory coupled to the simulation host processor and storing a first evaluation function for executing the simulation by the simulation host processor by calculating an evaluation value using a first parameter having a plurality of values and at least one second parameter having a plurality of values, wherein the simulation host processor is configured to
accept information for identifying the plurality of values of the first parameter and the plurality of values of the second parameter;

execute a first simulation by calculating a plurality of evaluation values corresponding to the plurality of values of the first parameter using the plurality of values of the second parameter and the first evaluation function;

acquire a result group including a plurality of evaluation values to which a predetermined phenomenon occurs from the plurality of evaluation values calculated by the first simulation;

acquire a start value and an end value of the first parameter for analyzing the predetermined phenomenon on the basis of the acquired result group;

execute a second simulation by calculating a plurality of evaluation values corresponding to the plurality of values of the first parameter from the acquired start value to the acquired end value using the plurality of values of the second parameter and the first evaluation function;

output data for displaying the plurality of evaluation values calculated by the second simulation in such a manner as to be continuous with the evaluation values in the acquired result group corresponding to the acquired start value;

hold a predetermined standard deviation of the result group to which the predetermined phenomenon occurs, in the memory;

divide the plurality of evaluation values calculated by the first simulation into result groups corresponding to the respective plurality of values of the second parameter;

calculate a standard deviation of the plurality of evaluation values for every value of the first parameter included in the plurality of result groups; and acquire the result group for which a standard deviation closest to the predetermined standard deviation has been calculated from the plurality of result groups, as a result group including the plurality of evaluation values to which the predetermined phenomenon occurs.

13. The simulation system according to claim 12, wherein the simulation host processor is further configured to acquire a first range of the evaluation values calculated by the first evaluation function at the end value;

extract the evaluation value corresponding to the end value and falling in the first range from the plurality of evaluation values calculated by the second simulation; and output, as a first control value, the value of the second parameter used to calculate the extracted evaluation value falling in the first range.

14. The simulation system according to claim 13, wherein the memory holds a second evaluation function other than the first evaluation function and that executes the simulation by calculating evaluation values using the first parameter and the second parameter, and the simulation host processor is further configured to acquire a second range of the evaluation values calculated by the second evaluation function at the end value;

identify the values of the second parameter corresponding to the acquired result group;

execute a third simulation by calculating a plurality of evaluation values corresponding to the plurality of values of the first parameter using the identified values of the second parameter and the second evaluation function;

execute a fourth simulation by calculating a plurality of evaluation values corresponding to the plurality of values of the first parameter from the acquired start value to the acquired end value in such a manner as to be continuous with the evaluation values calculated by the third simulation corresponding to the acquired start value using the plurality of values of the second parameter and the second evaluation function;

extract the evaluation value corresponding to the end value and falling in the second range from the plurality of evaluation values calculated by the fourth simulation;

identify, as a second control value, the value of the second parameter used to calculate the extracted evaluation value falling in the second range;

extract, as a third control value, the value of the second parameter that serves as the first control value and the second control value; and generate data for displaying the extracted third control value.

15. The simulation system according to claim 12, wherein the simulation host processor is further configured to accept information for identifying a plurality of combinations of the values of a plurality of the second parameters;

execute the first simulation by calculating a plurality of evaluation values corresponding to the plurality of values of the first parameter using the plurality of combinations of the values of the plurality of the second parameters and the first evaluation function;

acquire a result group including a plurality of evaluation values to which the predetermined phenomenon occurs from the plurality of evaluation values calculated by the first simulation;

identify a first combination of the values of the second parameters used to calculate the evaluation values included in the acquired result group;

generate a plurality of second combinations of the values of the second parameters for analyzing a sensitivity of each of the second parameters by changing the respective values of the second parameters included in the identified first combination;

acquire an analysis value of the first parameter determined to analyze the sensitivity;

identify the evaluation values in the acquired result group corresponding to the acquired analysis value;

execute a fifth simulation by calculating a plurality of evaluation values corresponding to the plurality of values of the first parameter using the plurality of second combinations and the first evaluation function;

calculate a sensitivity indicating a magnitude of an influence of each of the plurality of second parameters on a result of the fifth simulation on the basis of the plurality of evaluation values calculated by the fifth simulation;

determine at least one second parameter used in the second simulation on the basis of the calculated sensitivity; and execute the second simulation using the plurality of values of the determined second parameter and the first evaluation function.

16. The simulation system according to claim 15, wherein the simulation host processor is further configured to calculate a ratio of a change in the plurality of evaluation values in the acquired result group; and acquire the analysis value by determining the value of the first parameter highest in the calculated ratio of the change as the analysis value.

17. The simulation system according to claim 16, wherein the simulation host processor is further configured to identify a minimum value of the first parameter; and acquire the start value by determining, as the start value, a value smaller than the determined analysis value and larger than the minimum value of the first parameter.

18. The simulation system according to claim 12, wherein the values of the first parameter are time, and the simulation host processor is configured to execute the first simulation according to the time using the plurality of values of the second parameter and the first evaluation function.

19. A simulation method performed by a simulation system using a plurality of parameters,
    the simulation system including a simulation host processor and a memory,
    the memory storing a first evaluation function for executing the simulation by calculating an evaluation value using a first parameter having a plurality of values and at least one second parameter having a plurality of values,
    the simulation method comprising:
    a step of accepting, by the simulation host processor, information for identifying the plurality of values of the first parameter and the plurality of values of the second parameter;
    a step of executing, by the simulation host processor, a first simulation by calculating a plurality of evaluation values corresponding to the plurality of values of the first parameter using the plurality of values of the second parameter and the first evaluation function;
    a step of acquiring, by the simulation host processor, a result group including a plurality of evaluation values to which a predetermined phenomenon occurs from the plurality of evaluation values calculated by the first simulation;
    a step of acquiring, by the simulation host processor, a start value and an end value of the first parameter for analyzing the predetermined phenomenon on the basis of the acquired result group;
    a step of executing, by the simulation host processor, a second simulation by calculating a plurality of evaluation values corresponding to the plurality of values of the first parameter from the acquired start value to the acquired end value using the plurality of values of the second parameter and the first evaluation function;
    a step of outputting, by the simulation host processor, data for displaying the plurality of evaluation values calculated by the second simulation in such a manner as to be continuous with the evaluation values in the acquired result group corresponding to the acquired start value,
    wherein the memory also stores a predetermined standard deviation of the result group to which the predetermined phenomenon occurs;
    a step of dividing, by the simulation host processor, the plurality of evaluation values calculated by the first simulation into result groups corresponding to the respective plurality of values of the second parameter;
    a step of calculating, by the simulation host processor, a standard deviation of the plurality of evaluation values for every value of the first parameter included in the plurality of result groups; and
    a step of acquiring, by the simulation host processor, the result group for which a standard deviation closest to the predetermined standard deviation has been calculated from the plurality of result groups, as a result group including the plurality of evaluation values to which the predetermined phenomenon occurs.

20. The simulation method according to claim 19, comprising:
    a step of acquiring, by the simulation host processor, a first range of the evaluation values calculated by the first evaluation function at the end value;
    a step of extracting, by the simulation host processor, the evaluation value corresponding to the end value and falling in the first range from the plurality of evaluation values calculated by the second simulation; and
    a step of outputting, by the simulation host processor, as a first control value, the value of the second parameter used to calculate the extracted evaluation value falling in the first range.

21. The simulation method according to claim 20, wherein
    the memory stores a second evaluation function other than the first evaluation function and that executes the simulation by calculating evaluation values using the first parameter and the second parameter, and
    the method further comprises:
    a step of acquiring, by the simulation host processor, a second range of the evaluation values calculated by the second evaluation function at the end value;
    a step of identifying, by the simulation host processor, the values of the second parameter corresponding to the acquired result group;
    a step of executing, by the simulation host processor, a third simulation by calculating a plurality of evaluation values corresponding to the plurality of values of the first parameter using the identified values of the second parameter and the second evaluation function;
    a step of executing, by the simulation host processor, a fourth simulation by calculating a plurality of evaluation values corresponding to the plurality of values of the first parameter from the acquired start value to the acquired end value in such a manner as to be continuous with the evaluation values calculated by the third simulation corresponding to the acquired start value using the plurality of values of the second parameter and the second evaluation function;
    a step of extracting, by the simulation host processor, the evaluation value corresponding to the end value and falling in the second range from the plurality of evaluation values calculated by the fourth simulation;
    a step of identifying, by the simulation host processor, as a second control value, the value of the second parameter used to calculate the extracted evaluation value falling in the second range;
    a step of extracting, by the simulation host processor, as a third control value, the value of the second parameter that serves as the first control value and the second control value; and
    a step of generating, by the simulation host processor, data for displaying the extracted third control value.

22. The simulation method according to claim 19, comprising:
    a step of accepting, by the simulation host processor, information for identifying a plurality of combinations of the values of a plurality of the second parameters;
    a step of executing, by the simulation host processor, the first simulation by calculating a plurality of evaluation values corresponding to the plurality of values of the first parameter using the plurality of combinations of the values of the plurality of the second parameters and the first evaluation function;
    a step of acquiring, by the simulation host processor, a result group including a plurality of evaluation values to which the predetermined phenomenon occurs from the plurality of evaluation values calculated by the first simulation;
    a step of identifying, by the simulation host processor, a first combination of the values of the second parameters used to calculate the evaluation values included in the acquired result group;
    a step of generating, by the simulation host processor, a plurality of second combinations of the values of the second parameters for analyzing a sensitivity of each of the second parameters by changing the respective values of the second parameters included in the identified first combination;

a step of acquiring, by the simulation host processor, an analysis value of the first parameter determined to analyze the sensitivity;

a step of identifying, by the simulation host processor, the evaluation values in the acquired result group corresponding to the acquired analysis value;

a step of executing, by the simulation host processor, a fifth simulation by calculating a plurality of evaluation values corresponding to the plurality of values of the first parameter using the plurality of second combinations and the first evaluation function;

a step of calculating, by the simulation host processor, a sensitivity indicating a magnitude of an influence of each of the plurality of second parameters on a result of the fifth simulation on the basis of the plurality of evaluation values calculated by the fifth simulation;

a step of determining, by the simulation host processor, at least one second parameter used in the second simulation on the basis of the calculated sensitivity; and a step of executing, by the simulation host processor, the second simulation using the plurality of values of the determined second parameter and the first evaluation function.

23. The simulation method according to claim 22, comprising:

a step of calculating, by the simulation host processor, a ratio of a change in the plurality of evaluation values in the acquired result group; and a step of acquiring, by the simulation host processor, the analysis value by determining the value of the first parameter highest in the calculated ratio of the change as the analysis value.

24. The simulation method according to claim 23, comprising:

a step of identifying, by the simulation host processor, a minimum value of the first parameter; and a step of acquiring, by the simulation host processor, the start value by determining, as the start value, a value smaller than the determined analysis value and larger than the minimum value of the first parameter.

* * * * *